United States Patent

Heine et al.

[11] Patent Number: 5,815,241
[45] Date of Patent: Sep. 29, 1998

[54] BINOCULAR INDIRECT OPHTHALMOSCOPE INCLUDING A TILTED MIRROR

[75] Inventors: Helmut Heine, Herrsching; Anton Schneider, Geisenbrunn; Otto H. Schmidt, Herrsching, all of Germany

[73] Assignee: Heine Optotechnik GmbH & Co KG., Herrsching, Germany

[21] Appl. No.: 790,480

[22] Filed: Jan. 29, 1997

[30] Foreign Application Priority Data

Aug. 5, 1996 [DE] Germany .................. 296 13 549.6

[51] Int. Cl.⁶ ........................................ A61B 3/10
[52] U.S. Cl. ................................ 351/220; 351/221
[58] Field of Search ...................... 351/205, 220, 351/221

[56] References Cited

U.S. PATENT DOCUMENTS

| | | | |
|---|---|---|---|
| 3,582,191 | 6/1971 | Cohen | 351/221 |
| 3,963,329 | 6/1976 | Stumpf et al. | 351/221 |
| 4,684,227 | 8/1987 | Schmidt et al. | 351/205 |
| 5,223,863 | 6/1993 | Heine et al. | 351/205 |
| 5,333,018 | 7/1994 | Heine et al. | 351/221 |
| 5,394,201 | 2/1995 | Hauptli | 351/221 |

*Primary Examiner*—Huy Mai
*Attorney, Agent, or Firm*—Griffin, Butler, Whisenhunt & Szipl, LLP

[57] ABSTRACT

A binocular indirect ophthalmoscope has illumination optics which have a tilted mirror that can be substantially-linearly displaced, by use of a first control, perpendicular to a beam path of an illumination beam exiting the ophthalmoscope, and that can be independently pivoted, by use of a second control, about an axis perpendicular to the beam path of the illumination beam and perpendicular to a direction of linear displacement, the mirror directing light of the illumination beam onto a retina of a patient. First and second controls for linearly moving and pivoting a tilted mirror are coupled to each other in such a way that the second control can be held at a fixed position relative to a housing of an ophthalmoscope.

4 Claims, 4 Drawing Sheets

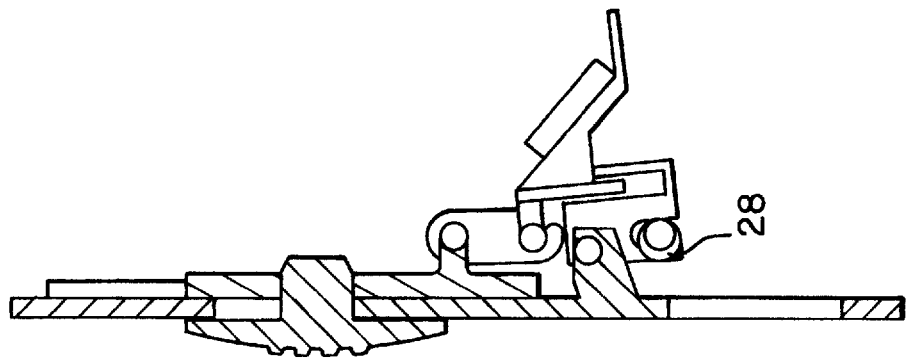
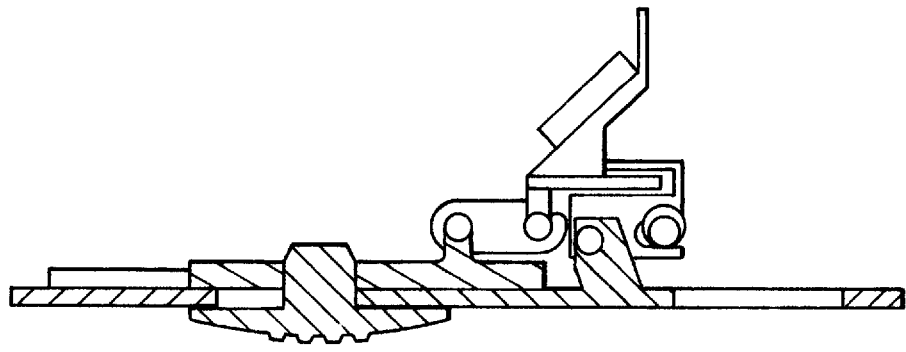
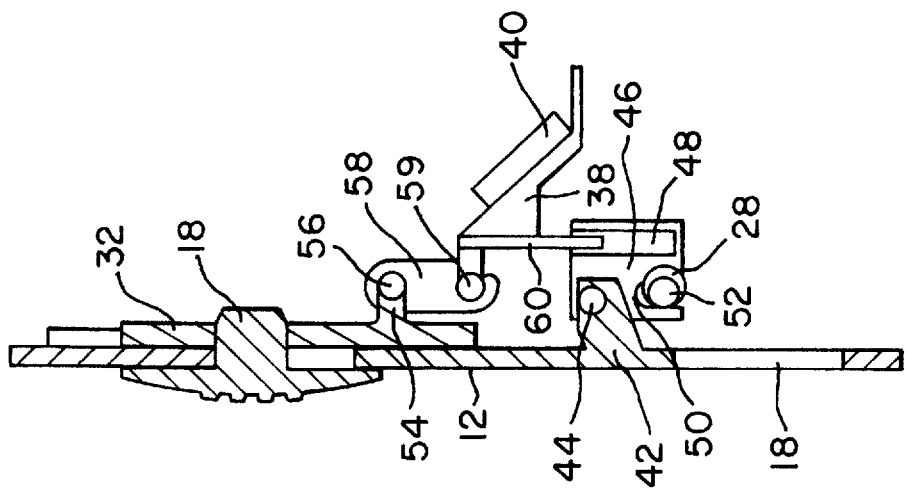

BINOCULAR INDIRECT OPHTHALMOSCOPE INCLUDING A TILTED MIRROR

BACKGROUND OF THE INVENTION

This invention relates to a binocular indirect ophthalmoscope, illumination optics of which have a tilted mirror that can be substantially-linearly displaced, by use of a first control, perpendicular to a beam path of an illumination beam exiting the ophthalmoscope, and that can be independently pivoted, by use of a second control, about an axis perpendicular to the beam path of the illumination beam and perpendicular to a direction of linear displacement, the mirror directing light of the illumination beam onto a retina of a patient.

Binocular indirect ophthalmoscopy is a procedure commonly used to examine a fundus oculi of an eye. The instrument used for this purpose contains an incandescent lamp, light from which is directed by means of illumination optics onto the eye that is to be examined. With aid of a focusing, or converging, lens held in front of a patient's eye by an examiner, the light is concentrated and directed through the patient's pupil onto the fundus of the eye. At the same time, the examiner observes an aerial view, or image, of the fundus of the eye, delineated by the focusing lens, through a binocular observation optics located beneath the illumination optics.

To achieve satisfactory illumination of an area of interest on the fundus of the eye, it is advantageous to be able to adjust the direction of the illumination beam vertically. To this end, in a usual embodiment of a binocular indirect ophthalmoscope, a tilted mirror is provided in the illumination optics which can be pivoted about its horizontal axis by means of a control.

In binocular indirect ophthalmoscopy, the illumination and observation beam paths must pass close together through the patient's pupil. This gives rise to strong reflexes from the concentrated light on the cornea, which hinder the examination. Attempts are made to avoid these reflexes through design measures, in that the illumination beam path is arranged as far as possible from the visual axis of the binocular part, i.e. from a plane of the observation beam path. However, this arrangement requires that the patient's pupil must be dilated by medication prior to examination with the binocular indirect ophthalmoscope.

For various reasons, this cannot be done in all patients, which means that opportunities to perform the examination are restricted.

As a remedial measure, in a binocular indirect ophthalmoscope known in the art of the type described above, a distance of an illumination beam from an axis of an observation beam path is adjustable between a position for dilated and a position for non-dilated pupils. In this arrangement, it is accepted that reflexes of corneas are stronger for non-dilated pupils than for dilated pupils. The distance of the illumination beam from the observation beam is modified through vertical displacement with the aid of a first control, generally in the form of a simple slide. A disadvantage of this design is that when a tilted mirror is displaced vertically, a second control used to pivot the tilted mirror is moved in the vertical plane, as well.

In the known device, this means that when one of the two controls of the tilted mirror is actuated, the other control can inadvertently be actuated as well. Moreover, the actuating apparatus to achieve this displacement is expensively designed. Specifically, the second control juts out from a housing of the device. Therefore, an opening in the form of a slit must be made in the housing, which means that an expensive dust gasket must be used at this location. Finally, the known device is susceptible to failure because the control that juts out from the housing can be easily broken off.

It is an object of this invention to provide a binocular indirect ophthalmoscope that has an uncomplicated design and is not substantially susceptible to failure.

SUMMARY

According to principles of this invention first and second controls for linearly moving and pivoting a titled mirror are coupled to each other in such a way that the second control can be held at a fixed position relative to a housing of an ophthalmoscope.

Preferably, a guide part with a guide element that runs approximately in a direction of linear displacement of the tilted mirror is coupled to the housing. The guide part can be pivoted by the second control. A cam or glider attached to the pivoted tilted mirror can be moved along a guide, which can be designed as a groove or bore hole.

The guide part is pivoted, preferably by a crank element actuated by the second control. In this design, the second control is preferably a shaft with an eccentric section, housed in an opening provided in the guide part.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIGS. 4a, 4b, and 4c are each a cross sectional view taken on a line IV—IV in FIG. 2, parallel to beam paths, showing actuating mechanisms for the tilted mirror.

DESCRIPTION OF THE PREFERRED EMBODIMENT

Figure 1:
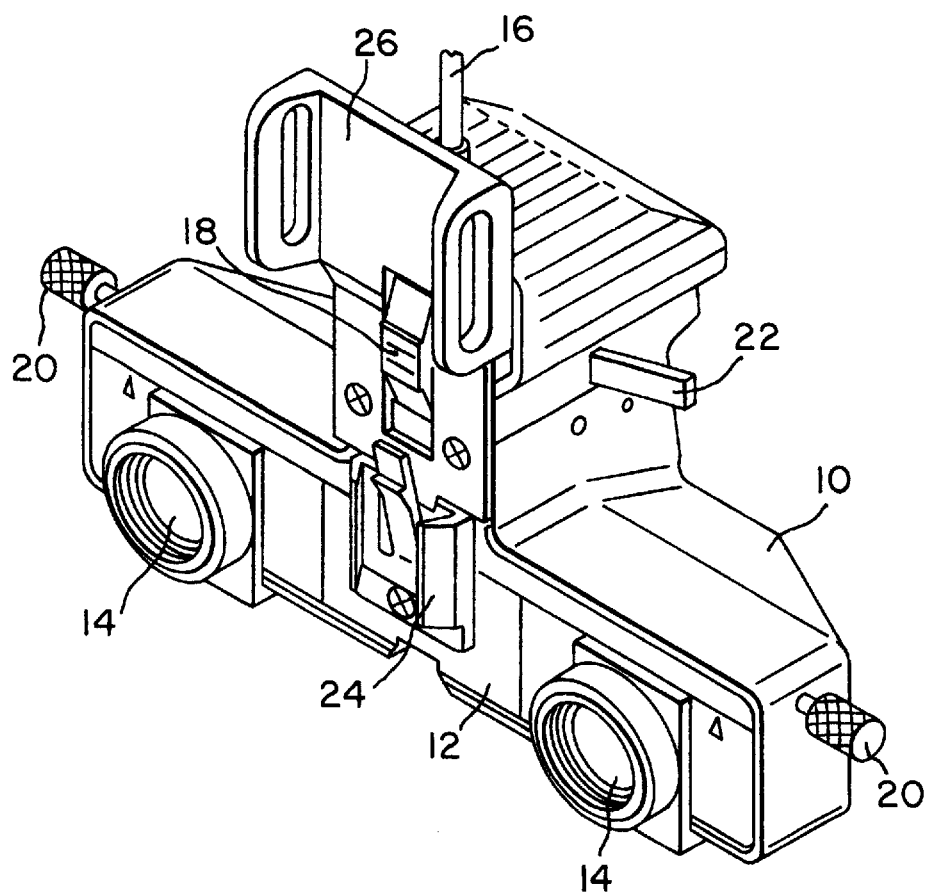
FIG. 1 is a perspective view of a binocular indirect ophthalmoscope having features of this invention, as seen from an exterior back wall thereof.

FIG. 1 shows a binocular indirect ophthalmoscope. Of elements of an observation beam path located in a lower area, two eyepieces 14 can be seen at a back wall 12 of a housing 10. The elements of an illumination beam path are located above the plane of an observation beam path. A cable 16 leads to a light bulb of an incandescent lamp (not shown) located at an upper portion of the housing 10; the lamp being placed above a tilted mirror 40 (not shown in FIG. 1) that can be displaced, by use of a slide 18, in a vertical plane and that is pivotal about a horizontal axis by use of adjusting knobs 20. The tilted mirror directs light of the light bulb forwardly onto an eye of a patient. The diameter of the illumination beam can be adjusted by means of an adjustable diaphragm (aperture), which is adjustable by means of a lever 22 that juts out through the housing 10.

On the back wall 12 of the housing 10, there are two additional mountings 24 and 26, the lower mounting 24 serving to attach the ophthalmoscope to a pair of glasses, the upper mounting 26 serving to attach the ophthalmoscope to a head band.

Figure 2:
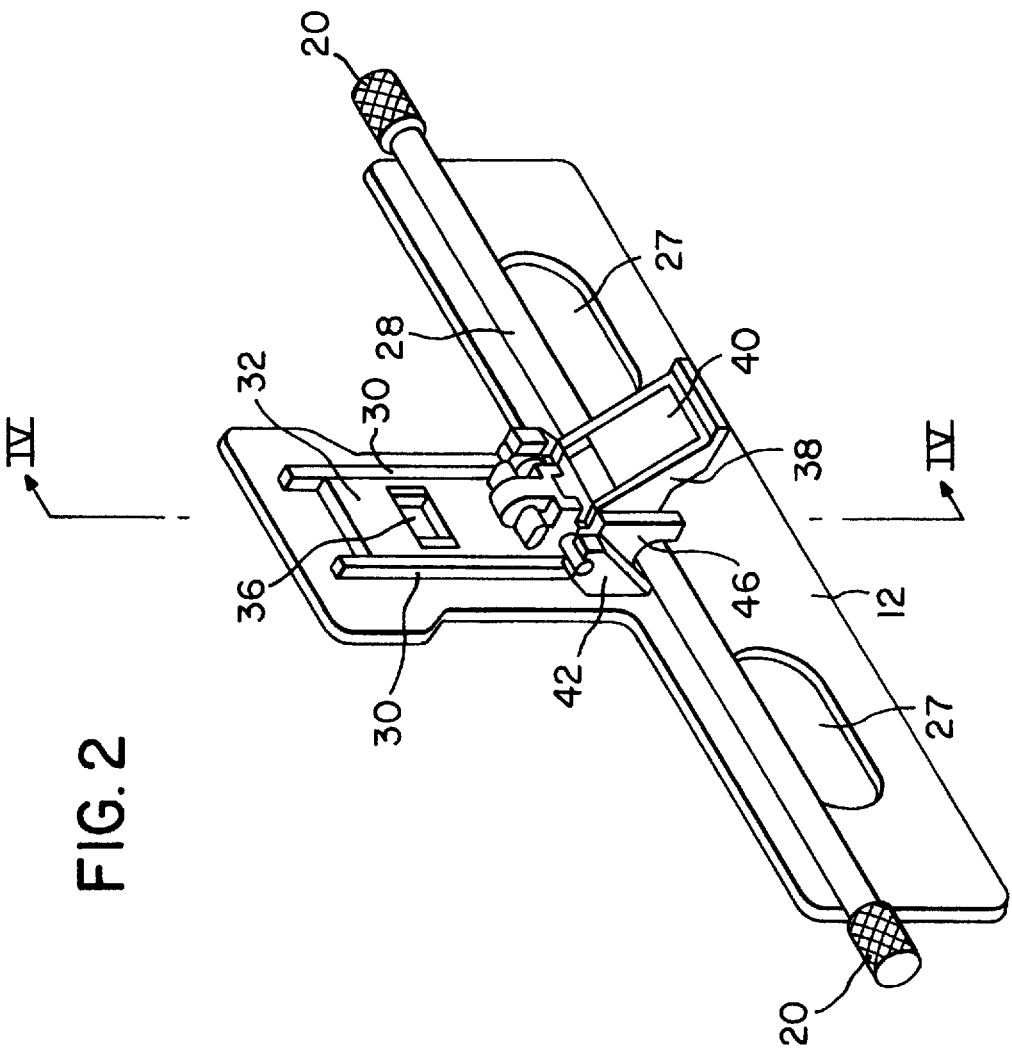
FIG. 2 is a perspective view of the back wall of the ophthalmoscope of FIG. 1 as seen from inside, with a tilted mirror.
Figure 3:
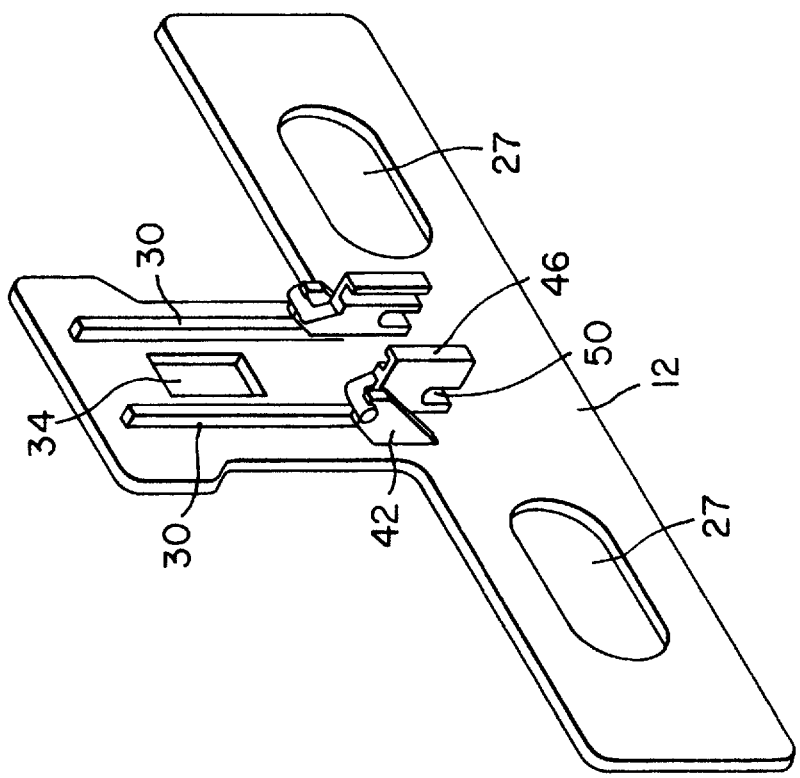
FIG. 3 is a perspective representation of the back wall, as in FIG. 2 but without the tilted mirror.

FIG. 2 shows a perspective representation of the back wall 12 of the ophthalmoscope (with two observation windows 27), to which a shaft 28 is attached by a bearing (not shown). The shaft 28 is substantially completely enclosed within the housing 10 with the exception of the two adjusting knobs 20 on its ends. The two adjusting knobs 20 allow a doctor to adjust the tilted mirror with either his left or right hand. Two guide rails 30 are on the back wall 12 above the shaft 28, between which a glider 32 is guided. The slide 18 shown in FIG. 1 extends through an opening 34 (FIG. 3) into an opening 36 in the glider 32, to which it is rigidly fastened. The glider 32 supports a mirror support 38, which can be pivoted by a few degrees from a middle position about an axis parallel to the back wall 12 and to the shaft 28. A tilted mirror 40 is attached to the mirror support 38.

An actuating mechanism used to displace the tilted mirror 40 is shown in greater detail in FIGS. 3 and 4a, 4b, and 4c. On an inner face of the back wall 12, two jibs 42 are positioned horizontally opposite one another, to each of which a guide part 46 is pivotally attached by means of a pin 44. On sides of the two guide parts 46 that face each other, guide grooves 48 are respectively provided, which, in the position shown in FIG. 4a, run roughly parallel to the back wall 12 and along the direction of displacement of the slide 18. Finally, a bottom of each of these guide parts 46 has a U-shaped slit 50. The shaft 28 has an eccentric section 52 in an area of the guide parts 46, which is surrounded by the U-shaped slit 50.

A jib 54 is attached to the glider 32 which can be adjusted in the vertical direction from outside by means of the slide 18; an upper end of a connecting rod 58 is attached to the jib 54 by a pin 56. At a lower end of the connecting rod 58, the mirror support 38, which supports the tilted mirror 40, is attached by means of a pin 59, and a slide 60 is attached to the mirror support. The two vertical outer edges of the slide 60 are placed in, and guided by, the guide grooves 48 opposite each other.

In place of the slide 60 attached to the mirror support 38, a cam could also be provided, that can be moved in a guide groove of a single guide part.

FIG. 4a shows the slide 18 in its uppermost position, in which the tilted mirror 40 is at its greatest distance from the plane of the observation beam path. This position is preferred for dilated pupils.

In FIG. 4b, the slide 18 is in its lowest position, thus very close to the plane of the observation beam path. In this position, examinations can be done when the pupil is at its normal size.

FIG. 4c shows the shaft 28 in a position that is rotated 180° with respect to its positions in FIGS. 4a and 4b, in which the cam 52 holds the guide parts 46 in a position pivoted by a few degrees.

In an ophthalmoscope pursuant to this invention, displacement of the tilted mirror by means of the first control (slide 18) is not transmitted to the second control (shaft 28), since a distance between the two controls is allowed to vary. Therefore the two controls can be displaced independently of each other. Since the position of the second control does not change with respect to the housing, a dust gasket in a opening through the housing can be uncomplicated in design.

The second control is substantially completely enclosed within the housing, except for short adjusting knobs that jut out from the housing.

The invention claimed is:

1. A binocular indirect ophthalmoscope, having a housing and illumination optics, the illumination optics including a means for directing an illumination beam along a first beam path and a tilted mirror (40) which forms an angle with the first beam path for intersecting the illumination beam and reflecting it along a second beam path for exiting said ophthalmoscope;

wherein the tilted mirror is linearly displaced by a first control (18) in a direction of linear displacement which is substantially perpendicular to the second beam path of the illumination beam, is independently pivoted by a second control (28) about an axis which is substantially perpendicular to the second beam path of the illumination beam exiting the ophthalmoscope and substantially perpendicular to the direction of linear displacement, and directs light of the illumination beam onto a retina of a patient;

a coupling mechanism for coupling the first and the second controls (18, 28) to each other in such a manner that the second control (28) can remain at a fixed position relative to the housing (10) of the ophthalmoscope while the first control linearly displaces the tilted mirror;

wherein said coupling mechanism includes a guide part (46) attached to the housing (10) with a guide groove (48) running in the direction of linear displacement of the titled mirror (40) for receiving and guiding a movable element (60) fastened to the tilted mirror (40), said guide part being pivoted by the second control (22) and said guide groove allowing linear movement of said moveable element relative to the guide part.

2. An ophthalmoscope as in claim 1, wherein the guide part (46) can be pivoted by a crank element (52) actuated by the second control (28).

3. An ophthalmoscope as in claim 2, wherein the second control is a shaft (28) and said crank element is an eccentric section (52) of the shaft (28) that is placed in an opening (50) in the guide part (32).

4. An ophthalmoscope as in claim 3, wherein the shaft (28) is substantially enclosed within the housing, with adjusting knobs (20) thereof extending out of the housing.

* * * * *